United States Patent
Humphrey et al.

(10) Patent No.: US 9,463,491 B2
(45) Date of Patent: Oct. 11, 2016

(54) AEROSOL PARTICLE SEPARATION AND COLLECTION

(71) Applicant: Hollison, LLC, Owensboro, KY (US)

(72) Inventors: Kevin E. Humphrey, Owensboro, KY (US); Anthony D. Bashall, Owensboro, KY (US)

(73) Assignee: Hollison, LLC, Owensboro, KY (US)

( * ) Notice: Subject to any disclaimer, the term of this patent is extended or adjusted under 35 U.S.C. 154(b) by 39 days.

(21) Appl. No.: 14/584,215

(22) Filed: Dec. 29, 2014

(65) Prior Publication Data

US 2015/0183003 A1    Jul. 2, 2015

Related U.S. Application Data

(60) Provisional application No. 61/921,666, filed on Dec. 30, 2013.

(51) Int. Cl.
| | |
|---|---|
| B07B 11/00 | (2006.01) |
| B07B 7/086 | (2006.01) |
| G01N 1/22 | (2006.01) |
| B07B 11/06 | (2006.01) |

(52) U.S. Cl.
CPC ............. *B07B 7/086* (2013.01); *G01N 1/2211* (2013.01); *B07B 11/06* (2013.01)

(58) Field of Classification Search
CPC ....... B07B 7/086; B07B 11/02; B07B 11/04; B07B 11/06; G01N 1/2211; G01N 1/2202; G01N 2001/2217; G01N 1/2208
See application file for complete search history.

(56) References Cited

U.S. PATENT DOCUMENTS

| | | | |
|---|---|---|---|
| 3,690,837 A * | 9/1972 | Witz et al. ........... | G01N 1/2202 422/52 |
| 4,012,209 A | 3/1977 | McDowell et al. | |
| 4,056,969 A * | 11/1977 | Barringer ................ | G01V 5/02 250/255 |
| 4,523,990 A * | 6/1985 | Duyckinck ............. | B07B 7/083 209/138 |
| 4,900,445 A | 2/1990 | Flanigan et al. | |
| 4,923,491 A | 5/1990 | Lawless et al. | |
| 4,969,934 A | 11/1990 | Kusik et al. | |
| 5,011,517 A | 4/1991 | Cage et al. | |
| 5,062,870 A | 11/1991 | Dyson | |
| 5,120,431 A * | 6/1992 | Cordonnier ............ | B07B 7/083 209/135 |
| 5,123,939 A * | 6/1992 | Morin .................... | B01D 45/12 55/459.1 |

(Continued)

FOREIGN PATENT DOCUMENTS

GB    2254024 A1    9/1992

OTHER PUBLICATIONS

United States Patent and Trademark Office; The International Search Report and Written Opinion; Search Report and Written Opinion; Apr. 22, 2015; pp. 1-14; Serial No. PCT/US2014/072515; United States Patent and Trademark Office as the International Searching Authority; US.

*Primary Examiner* — Joseph C Rodriguez
(74) *Attorney, Agent, or Firm* — Wyatt, Tarrant & Combs, LLP; Stephen C. Hall

(57) ABSTRACT

A contactor is positioned coaxially with and substantially within at least one separator, and otherwise is configured to receive aerosolized target particles of interest as a sample. The use of a plurality of separators that are coaxial with each other and the contactor increases the number of separations involving target particles and other constituents of air at a sampling point, whereby in some embodiments the separators are rotatably configurable relative to each other and to the contactor.

12 Claims, 8 Drawing Sheets

(56) References Cited

U.S. PATENT DOCUMENTS

| | | |
|---|---|---|
| 5,679,580 A | 10/1997 | Ball et al. |
| 5,690,709 A | 11/1997 | Barnes |
| 5,861,316 A | 1/1999 | Cage et al. |
| 5,988,603 A | 11/1999 | McCampbell et al. |
| 6,103,534 A * | 8/2000 | Stenger ............... G01N 21/76 422/52 |
| 6,355,178 B1 | 3/2002 | Couture et al. |
| 6,468,330 B1 | 10/2002 | Irving et al. |
| 6,843,103 B2 | 1/2005 | Aguilera et al. |
| 7,108,138 B2 | 9/2006 | Simpson |
| 7,281,440 B2 | 10/2007 | Graze, Jr. et al. |
| 7,310,992 B2 | 12/2007 | Swank et al. |
| 7,347,112 B2 | 3/2008 | Kay |
| 7,549,349 B2 | 6/2009 | Swank et al. |
| 7,647,811 B2 | 1/2010 | Wei et al. |
| 7,807,344 B2 | 10/2010 | Dodd |
| 7,964,018 B2 * | 6/2011 | Kang .................... B01D 45/12 95/13 |
| 8,167,986 B2 | 5/2012 | Schneider et al. |
| 8,186,235 B2 | 5/2012 | Mainelis |
| 8,188,874 B2 | 5/2012 | Calio |
| 8,272,279 B2 * | 9/2012 | Bodily ................ G01N 1/2211 73/863.21 |
| 8,323,383 B2 | 12/2012 | Evans et al. |
| 8,875,589 B1 | 11/2014 | Mancinho et al. |
| 9,028,758 B2 * | 5/2015 | Keinan ............... G01N 1/2211 422/86 |
| 9,335,236 B2 | 5/2016 | Bry et al. |
| 2006/0115908 A1 | 6/2006 | O'Brien |
| 2007/0251386 A1 | 11/2007 | Swank et al. |
| 2007/0256476 A1 | 11/2007 | Swank et al. |
| 2007/0295208 A1 | 12/2007 | Fairchild |
| 2008/0198382 A1 * | 8/2008 | Otjes .................... G01N 1/2205 356/438 |
| 2010/0015601 A1 | 1/2010 | Gilmore et al. |
| 2012/0202210 A1 | 8/2012 | Burroughs et al. |
| 2013/0260397 A1 | 10/2013 | Biselli et al. |
| 2014/0130615 A1 * | 5/2014 | Karki ..................... F23N 5/003 73/863.21 |
| 2016/0116390 A1 * | 4/2016 | Tan ...................... G01N 1/2211 73/28.04 |

* cited by examiner

- 110: Unseparated constituents are transferred along a defined path within conduit
- 12, 14, 16
- 18: Aerosolized particulate
- 100: Bulk materials pass sampling point
- 120: Unseparated constituents enter at least one separator
- 130: Target particles enter contactor
- 140: Reservoir delivers carrier liquid to contactor
- 150: Target particles/carrier liquid enter collection vial
- 11, 17, 40, 42, 45
- Network / controller

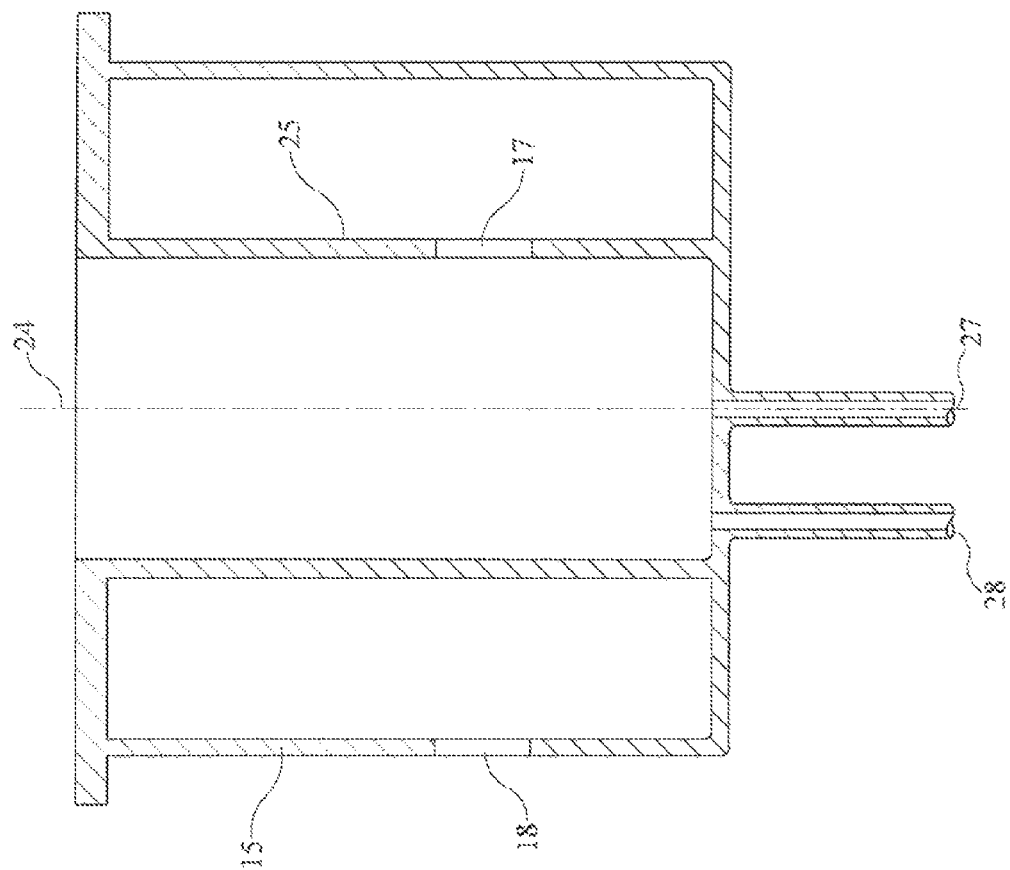

AEROSOL PARTICLE SEPARATION AND COLLECTION

CROSS REFERENCE TO RELATED U.S. APPLICATION

This application claims the benefit of priority to U.S. Provisional Application No. 61/921,666, which was filed on Dec. 30, 2013.

FIELD OF INVENTION

The embodiments disclosed herein relate to separating and collecting a concentrated sample of matter from aerosolized particles in the atmosphere at a sampling point.

BACKGROUND

In commerce, many goods are sold as bulk materials. The term "bulk materials" refers to items obtained, transported, used, stored, or handled in a group, non-limiting examples of which include grain, wheat, vegetables, tea, spices, flavorings, peanuts, coffee beans, soybeans, and other agricultural products; manufactured food products (including human food and pet food products); pharmaceutical products; health products like multivitamins and supplements. Packages which are handled and shipped are also an example of bulk materials according to the descriptions and teachings herein. Each example is an item that can be broken down into individual units and grouped with numerous others of its kind for shipment.

There is a need to sample bulk materials to determine if they contain any matter that causes injury, disease, or irritation if inhaled or ingested by a person or absorbed through the skin, or matter that creates a risk of combustion or explosion, either by itself or in contact with other matter. Such matter is characterized in different ways, and depending on its nature may be referred to variously as contaminants, adulterants, pathogens, viruses, bacteria, microorganisms, fungi, toxins, toxic chemicals, and pollutants. For brevity, such examples of matter set forth in this paragraph are referred to herein as "contaminants."

Alternatively, a need exists to sample bulk materials to determine if they contain matter that is desirable and beneficial, i.e., which is supposed to be present. Such substances include, again by way of illustration only, an additive used to enhance a manufacturing process related to a particular commodity; or matter incorporated with a particular commodity providing beneficial, nutritional, or therapeutic effects, such as proteins, nanoparticles, and additives. For brevity, all such substances contemplated by this paragraph are referred to, individually and collectively, as "additives."

In the past, various attempts have been made involving the separation and collection of particulate matter, for the purpose of obtaining a concentrated sample that can be analyzed, tested, or further studied to determine the quality of bulk materials. In some cases, the bulk materials have been related to food, while in other contexts separation and collection have been performed on non-food bulk materials. The present embodiments are not limited to the type of bulk materials which they can be practiced upon.

When contaminants are present in bulk materials, the contamination will be borne on microscopic particles of matter in the atmosphere located near the bulk materials. Such particles exist, for example, in the interstitial headspace between individual units of the bulk materials. The same is true of additives. The particles that bear the contaminants or additives (i.e., a biological or chemical compound of interest) are referred to herein as target particles. A target particle generally can be any matter that needs to be sampled, detected, or analyzed, such as by using polymerase chain reaction, high performance liquid chromatography, gas chromatography-mass spectrometry, and immunoassaying to name a few non-limiting examples. Thus, target particles are those particles that are joined to any compound or matter which is either beneficial to, or detrimental to, the formulation, nutritional value, therapeutic value, efficacy, integrity, safety, or edibility of bulk materials. Illustrative examples of such compounds or matter include, but are not limited to, that which may cause injury, disease, or irritation if inhaled or ingested into the system or absorbed through the skin; or that may create a risk of combustion or explosion, either by itself or in contact with other matter, or that may react with other matter to produce unwanted chemical reactions; or an additive used to enhance a manufacturing process; or matter providing beneficial, nutritional, or therapeutic effects.

Various approaches have been tried before with respect to the collection of target particles, including the separation of target particles. One problem that these approaches have attempted to overcome, largely unsuccessfully, involves increasing the selectivity so that a collected sample contains a higher concentration of target particles because of the removal of other particles. Accordingly, if one focuses substantially on collection to the substantial exclusion of separation, it results in a collected sample without a sufficiently high concentration of target particles to make detection effective. To try to overcome this limitation, some have tried filters, screens, or the like upstream of the contactor device, but such approaches have resulted in the filters and screens becoming clogged with particles that limits the usefulness of the system. Thus, an approach is needed that accomplishes both separation and collection, and which can be flexibly configured so it can be useful in a variety of contexts in the collection and separation of a number of different target particles depending on the situation.

SUMMARY

The present embodiments which are described and claimed herein relate to separating various particles in the form of aerosolized (liquid or solid) particulate, which are in the vicinity of certain bulk materials. Collectively, particles of matter drawn from a sampling point into at least one separator are referred to as constituents herein. However, not all of the constituents are target particles. That is, particles which are unlikely to bear biological or chemical compounds of interest during later testing and detection need to be separated from the target particles. Rather, target particles are ones upon which, due to their sizes and densities, contaminants or other biological or chemical compounds of interest are likely to be located. The present embodiments collect these target particles in a concentrated form. One or more separations of particles based on their respective densities may occur before the target particles enter a contactor, where the target particles are dispersed in a liquid for collection.

Examples of contaminants and additives according to present embodiments were provided in the Background, but by no means are these limiting. The present embodiments relate to many types of target particles. The scope of the embodiments described and/or claimed herein is not limited by the specific type of target particle to be collected. Collectively, the target particles and the other particles are referred to as constituents, all of which are found in aerosolized form in the interstitial headspace around the bulk materials.

Systems and methods according to multiple embodiments and alternatives herein comprise at least one separator arranged coaxially with a contactor positioned substantially within the at least one separator. The at least one separator is in fluid communication with a sampling point, e.g., a location of a manufacturing facility where bulk materials undergo sampling. The at least one separator and the contactor are also in fluid communication. In certain embodiments, the at least one separator comprises a substantially enclosed volume defining a chamber. The contactor comprises a substantially enclosed volume defining a contact space, i.e., an area in which target particles are contacted by a carrier liquid and transferred out of the contactor into a collection vessel, e.g., a vial with or without a removable cap is a non-limiting example of a collection vessel.

In certain embodiments, a fan or blower (for brevity, fan) generates negative pressure sufficient to transfer constituents from a sampling point into the at least one separator. It will be understood in this sense that the fan should be at an appropriate setting to generate a vacuum that draws air, gas, and constituents toward it. Constituents, including target particles, are generally aerosolized meaning they are dispersed as fine particles or liquid droplets throughout a gas, for example the atmosphere at a sampling point, and are carried along in the air that is drawn toward the fan. However, the act of transferring constituents from the interstitial headspace around the bulk materials at the sampling point necessarily introduces particles other than the target particles into the collection system. Such other particles of matter making up the constituents may include dust or other particles generally found at a sampling point for a specific type of facility. The at least one separator separates at least some of these other particles from the target particles.

Due to a rotational gas movement pattern established within the at least one separator, a centrifugal force is exerted upon the aerosolized constituents. The constituents' momentum and overall response to this force is related to their respective sizes and densities. For constituents which are larger and more dense, greater radial momentum is established away from the center of the at least one separator, as represented by a central (virtual) axis. Conversely, constituents that are smaller and less dense are not urged radially outward to such an extent.

The contactor is positioned substantially within the at least one separator, and the two are coaxial. A contactor opening 17 is formed in the contactor such that constituents colliding with the at least one separator may enter the at least one separator through that opening 17. Within the at least one separator, the gas movement pattern is configured to selectively allow target particles through the contactor opening 17 based on their sizes and densities, while forcing larger and heavier constituents away from the central axis and the contactor opening 17, thereby preventing those other, larger and heavier constituents from entering through such contactor opening into the contactor. Conversely, smaller, lighter target particles are capable of making contact with the contactor opening 17 and entering the contactor through that opening, because the centrifugal force established by the gas movement pattern does not direct them outward and away from the central axis.

Accordingly, fractions reaching the contactor contain a higher concentration of target particles compared to the makeup of all the constituent particles at a sampling point. In the contactor, target particles are contacted with and dispersed within a carrier liquid before exiting the contactor through an outlet. In some embodiments, a vacuum is configured to generate negative pressure within the contactor, the at least one separator, and at the sampling point, and the geometries of the at least one separator and contactor create the rotational gas movement pattern described herein. The force of the vacuum is sufficient to transfer constituents from the sampling point to the separators and then to the contactor. Alternatively, sufficient positive pressure is exerted at the sampling point, for example by a positive pressure fan which urges constituents generally in a direction of first conduit opening 14 and then along a transfer path inside conduit 12, into at least one separator 15 via inlet 18 where the constituents are subjected to a rotational gas movement pattern, causing some constituents to enter contactor 25 via opening 17, while excluding other constituents from the contactor based on differences in their sizes and densities.

In certain embodiments, a plurality (two or more) of separators is used, each being configured coaxially with the others and with the contactor. The outermost one of the plurality of separators is in closer proximity to, and therefore in more direct fluid communication with, the sampling point. The other separator(s) are then arranged successively interiorly between the outermost separator and the contactor. Each separator and contactor is in fluid communication (at least indirectly) with the spaces defined by all other separators, with the space defined by the contactor, and with the sampling point. Consequently, the vacuum establishes a rotational gas movement pattern within the spaces defined by each separator and contactor.

Being arranged in this way, it is possible to achieve a series of separations according to the respective densities of constituents in the plurality of separators and before the aerosolized target particles enter the contactor. Because the concentration of target particles is higher within the contactor than within the separator(s), detection of target particles in the concentrated sample is more effective. In certain embodiments, two or more separators are rotatably adjusted according to an alignment configuration to provide a series of separations before target particles enter the contactor. The respective openings 19 are configured in an alignment relative to every other opening 19 and relative to the inlet 18, all of which are likewise positioned relative to contactor opening 17 of the contactor.

Once the concentrated sample containing target particles is obtained, it can be handled as selectably desired by a user, e.g., by testing, or screening the contents of this sample. However, the embodiments describe and/or claimed herein are not limited by how the concentrated sample is handled once obtained in a collection vessel.

BRIEF DESCRIPTION OF THE DRAWINGS

The drawings and descriptions herein are to be understood as illustrative of structures, features, processes, and aspects of the present embodiments and do not limit the scope of the embodiments. Accordingly, the scope of the embodiments described and/or claimed herein is not limited to the precise arrangements or scale as shown in the drawing figures.

FIG. 1C is a schematic figure with a representation of constituent particles of matter in proximity to a sampling point.

FIG. 1D is a schematic figure of an aerosol particle separation and collection system, according to multiple embodiments and alternatives.

FIG. 3 is a cross-section view of an aerosol particle separation and collection system having at least one separator and a contactor configured coaxially, across line 3-3 of FIG. 2, according to multiple embodiments and alternatives.

MULTIPLE EMBODIMENTS AND ALTERNATIVES

Figure 2:
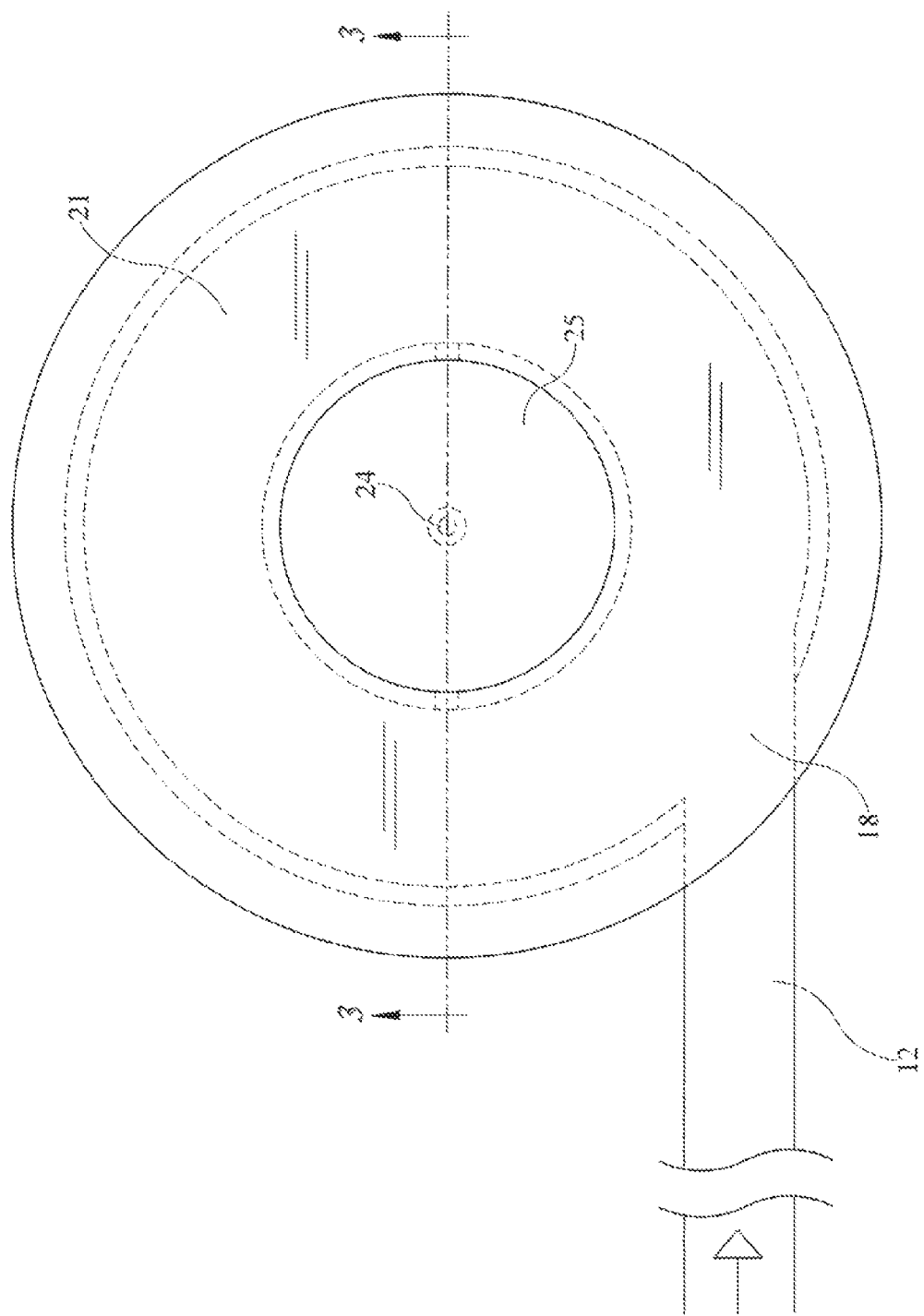
FIG. 2 is a top perspective view of an aerosol particle separation and collection system having at least one separator and a contactor configured coaxially, according to multiple embodiments and alternatives.

In certain embodiments, and as illustrated generally throughout the drawing figures, an aerosol particle separation and collection system comprises at least one separator 15 arranged for fluid communication with a sampling point 20 by way of an inlet 18; and a contactor 25 configured coaxially with the at least one separator about a common vertically-oriented central axis 24, the contactor being smaller than and positioned substantially within the at least one separator. Two or more objects are coaxial if the structure of the objects is defined at least in part by walls having inner and outer surfaces, with the objects being situated around a common central axis and the outer wall surface of one object being substantially the same shape but of smaller size than an inner wall surface of a second object (and of a third object, a fourth object, and so on depending on the number of objects which are coaxial). In some embodiments, the at least one separator 15 comprises a chamber 21 (FIG. 2) and has a curved inner wall surface 22, while contactor 25 comprises a separate chamber as a contact space and has a curved outer wall surface 23 (see FIG. 4A for surfaces 22, 23). Although illustrated in FIG. 2 as circular, the curvature of wall surfaces 22, 23 can be any of a number of geometries, including oval, elliptical, and teardrop to name a few non-limiting examples in addition to circular. Because the at least one separator and the contactor are substantially enclosed chambers, dashed lines are used to depict these interior curved wall surfaces. The contactor 25 is in fluid communication with the at least one separator by way of a contactor opening 17 formed in the surface of the contactor.

Figure 1A:
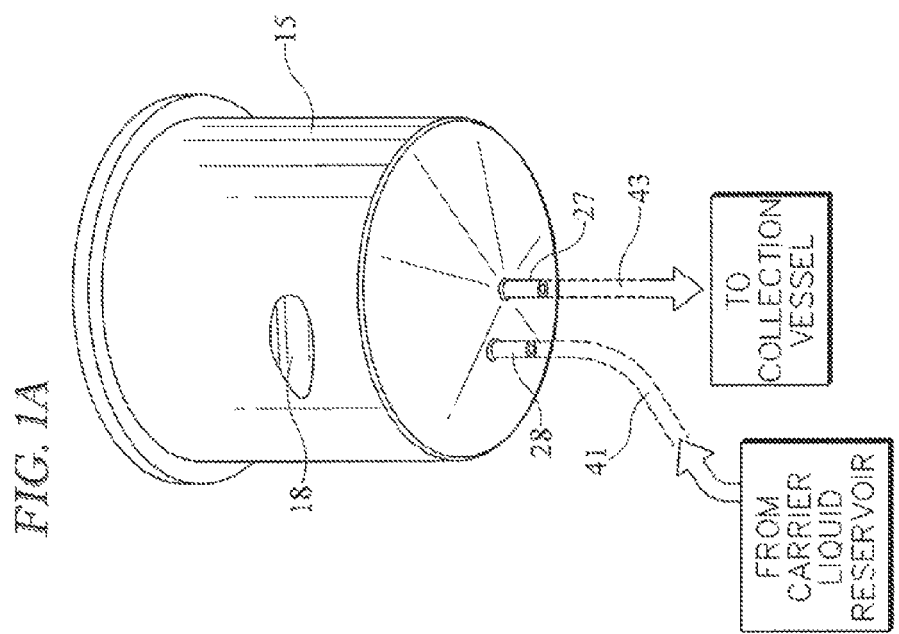
FIG. 1A is a side elevation view of an aerosol particle separation and collection system, according to multiple embodiments and alternatives.
Figure 1B:
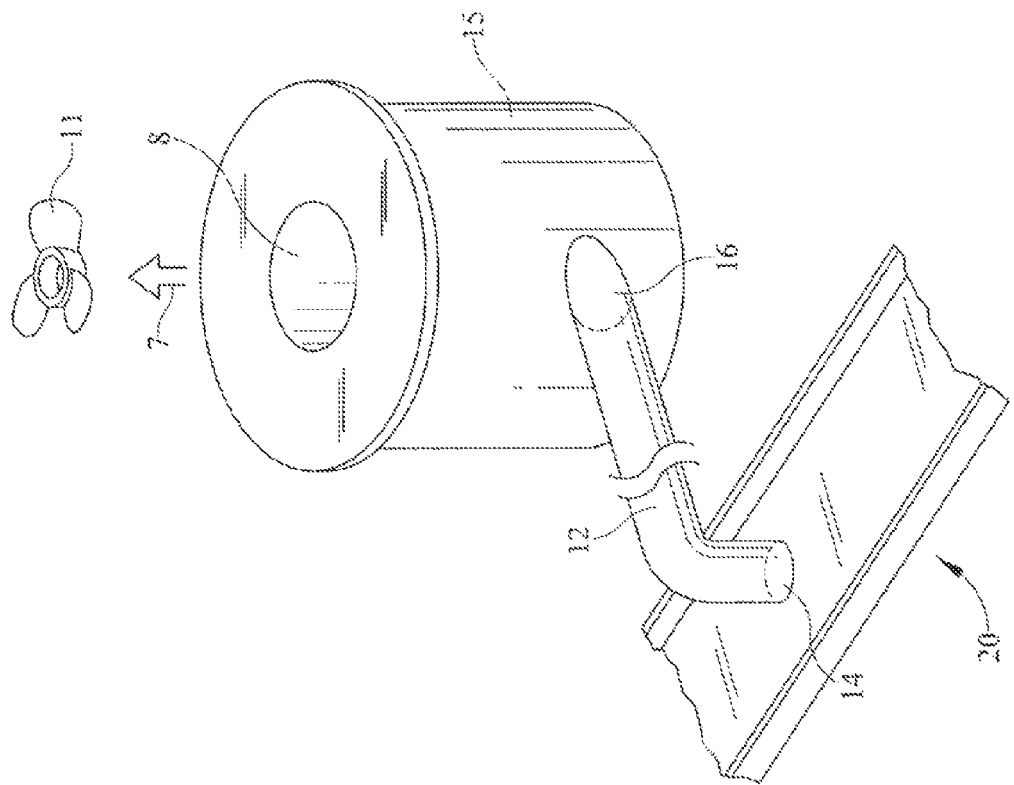
FIG. 1B is a perspective view of an aerosol particle separation and collection system, according to multiple embodiments and alternatives.
Figure 4B:
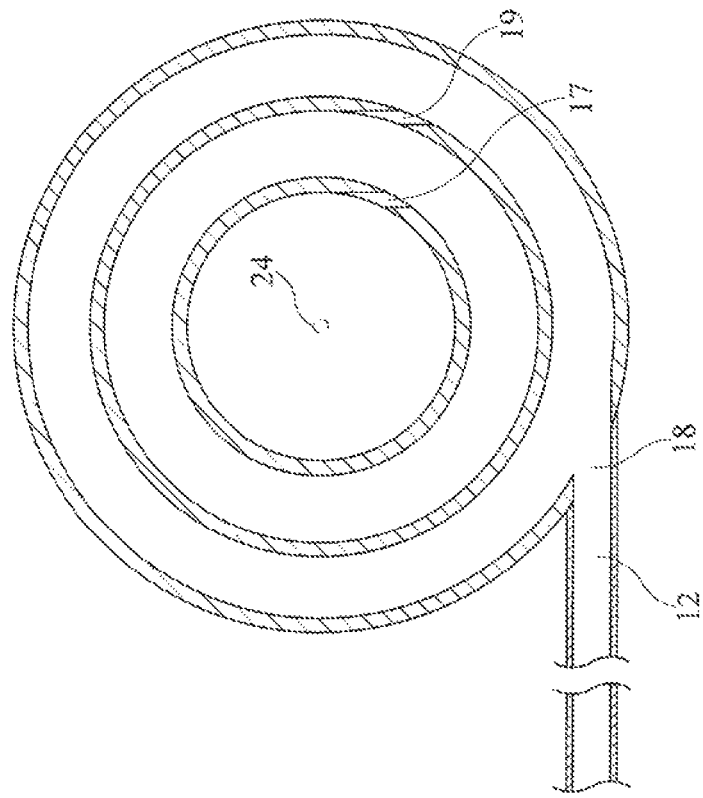
FIG. 4B is a top perspective sectional view of an aerosol particle separation and collection system having a plurality of separators and a contactor configured coaxially, according to multiple embodiments and alternatives.
Figure 4A:
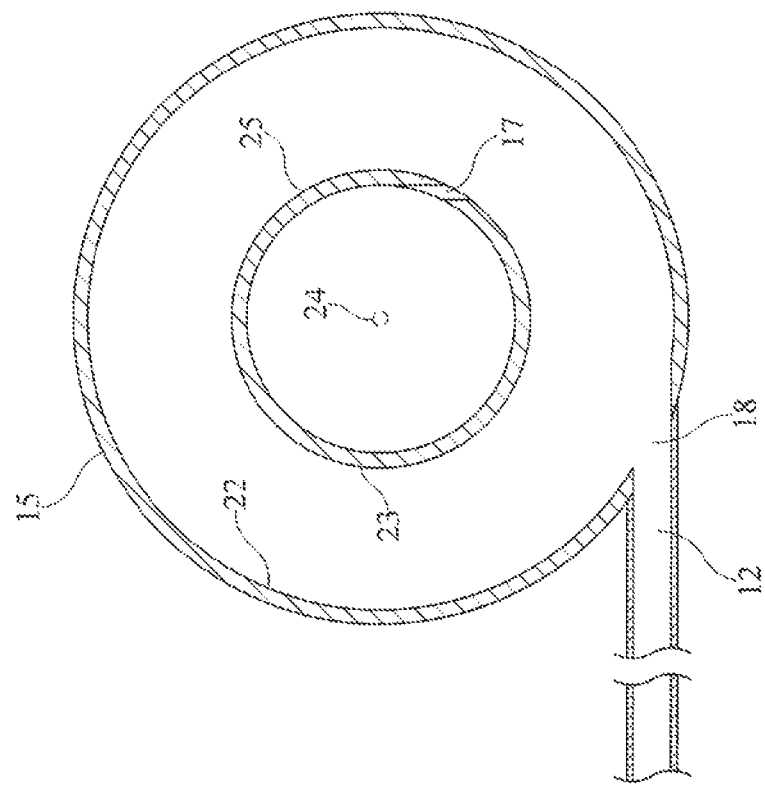
FIG. 4A is a top perspective sectional view of an aerosol particle separation and collection system having at least one separator and a contactor configured coaxially, according to multiple embodiments and alternatives.

Turning to FIG. 1B, in some embodiments, a fan 11 generates a vacuum which draws a force in a direction indicated by arrow 7. Contactor opening 17 and inlet 18 (as seen in FIG. 4B and others) thus establish fluid communication of the system with conduit 12, whereby the force generated by negative pressure of fan 11 is exerted through the conduit and at the sampling point 20. A vacuum opening 8 is formed in a surface of contactor 25 into which a hose (not shown) attached to fan 11 snugly fits, creating a draw from the fan that acts within the contactor, separator(s), and at the sampling point. Ultimately, as they make their way into contactor 25, target particles are separated from other constituents that were also transferred from the sampling point 20. Inside contactor 25, target particles are dispersed in a liquid, and the liquid-borne target particles exit the contactor through outlet 27 as shown in FIG. 1A. In some embodiments, at least one separator 15 and contactor 25 are cylindrically shaped, with the contactor being smaller than and positioned substantially within the at least one separator(s) 15.

Figure 1C:
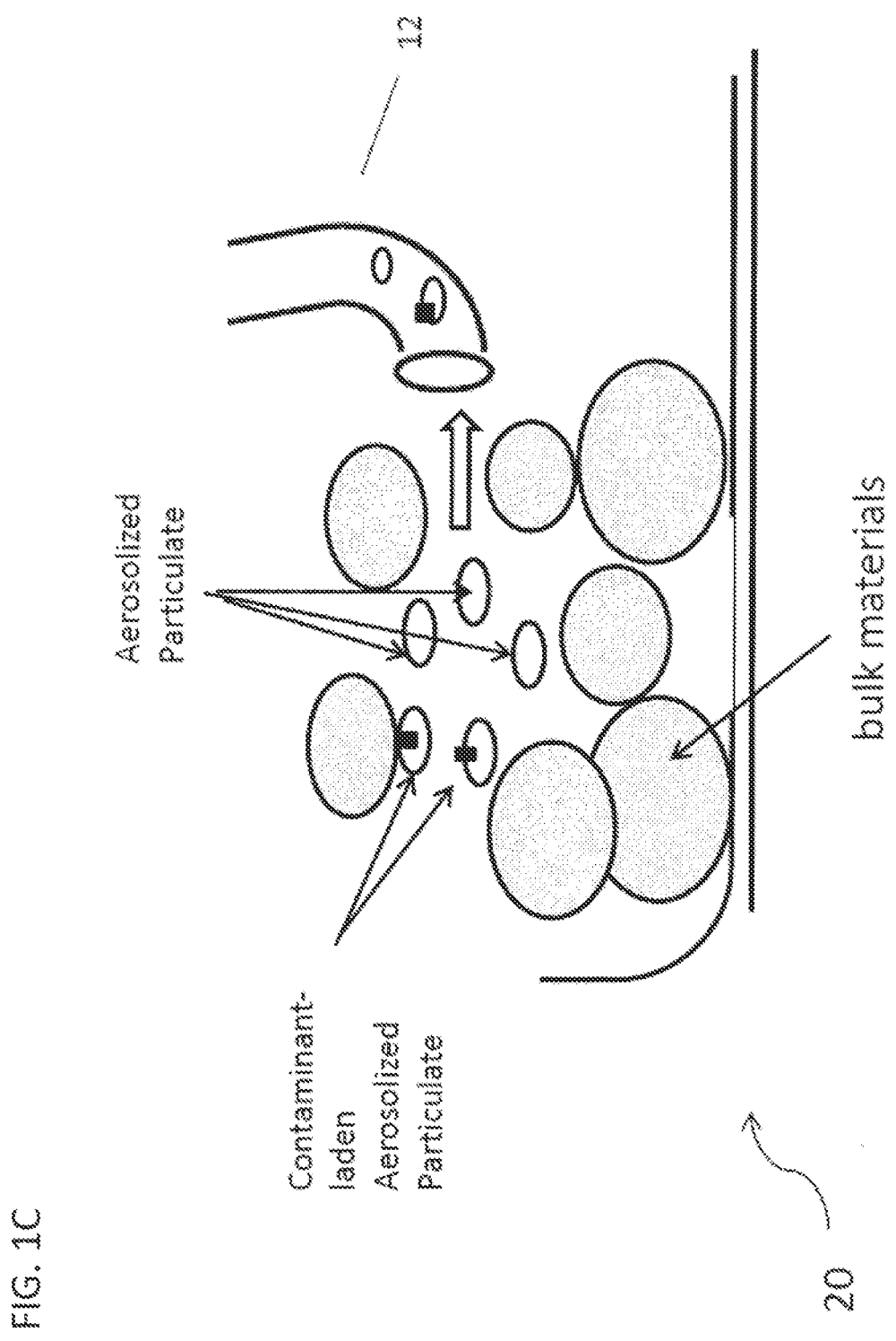

FIG. 1C and FIG. 1D are schematic figures, which are not indicative of any spatial relationships regarding the system components, nor of their geometric shape, but rather reflect the flow of target particles and other constituents through the system. FIG. 1C represents a sampling point 20 which bulk materials move past—in proximity to conduit 12. Constituents, including target particles, are in the interstitial headspace surrounding the bulk materials, and are urged in the direction indicated by the arrow thus entering the separation and collection system via conduit 12 at its first end. Constituents exist as aerosolized particulate, some of which will be laden with contaminant if there is contamination existing in the bulk materials.

FIG. 1D represents various system components beginning at step 100 where bulk materials pass a sampling point. As unseparated constituents enter conduit 12, they are transferred from sampling point 20 at step 110. At step 120, these unseparated constituents enter at least one separator through inlet 18. Next, at step 130, some of the constituents in the form of aerosolized particular matter, including target particles, enter the contactor through contactor opening 17. At step 140, carrier liquid is delivered from reservoir 40 to the contactor. The target particles are dispersed in the carrier liquid inside the contactor, which is then delivered to collection vial 42 at step 150 for any sort of physical, chemical, or biological testing or detection as may be chosen.

Now turning back to FIG. 1A and FIG. 1B, at least one separator 15 is in fluid communication with a sampling point 20 via transfer conduit 12. In some embodiments, conduit 12 is formed from piping having a first conduit opening 14 and a second conduit opening 16. Conduit 12 defines a substantially closed (save for first and second openings) for constituents to be transferred from sampling point 20 to at least one separator 15, the latter being entered through an inlet 18 joined to second conduit opening 16. In a sample configuration, first opening 14 of conduit 12 is exposed to the atmosphere at a sampling point 20, for example a conveyor line or portion of a production line where bulk materials pass.

Figure 5:
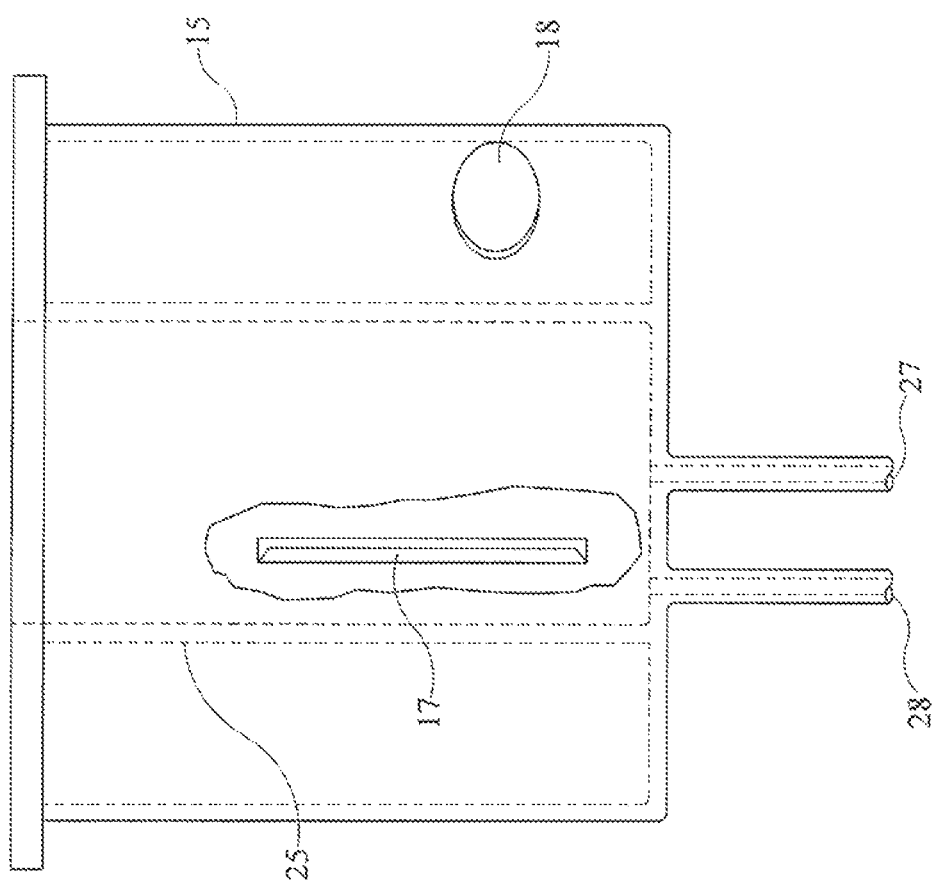
FIG. 5 is a perspective view with cutaway of an aerosol particle separation and collection system, according to multiple embodiments and alternatives.

In certain embodiments, conduit 12 including conduit opening 16 is oriented tangentially to the separator as shown in FIG. 1B. In this sense, tangentially means offset, i.e., not perpendicular to central axis 24 along a transverse (horizontal) plane of the at least one separator. Although present embodiments are not limited to a specific shape of the inlet, FIG. 5 shows inlet 18 (providing access into the outermost separator) with a substantially elliptical geometry as result of the tangential offset of second opening 16. In some embodiments, inlet 18 is joined to and sealed with conduit 12 at its second opening 16 using connectors, gaskets, snaps, or other connecting apparatuses known in the art. Alternatively, at least a portion of conduit 12 that includes second end 16 is formed integrally with separator 15 with its inlet 18 and the second end 16 of the conduit joined at fabrication. Accordingly, it will be appreciated that the tangential orientation of the conduit relative to the central axis 24 conserves the momentum of constituents long enough (compared to a perpendicular entry angle) to promote a centrifugal gas movement pattern within the separator, and to separate constituent particles according to density. In non-limiting fashion, and depending on the particular circumstances, an airflow rate for establishing a suitable gas movement pattern within the contactor and separator(s) will range from about 50 to 1,500 liters/minute.

Also not meant as limiting, a food production facility is one example of an application where such embodiments could be used. Some foods are processed in such a facility from various ingredients, which are used in making the food. If any ingredient contains target particles, e.g., due to contamination, such contamination will be borne on specific particles which are referred to herein as target particles, and these will be found in the atmosphere at various points in the production line. The first opening 14 of conduit 12 is thus exposed to the atmosphere at a sampling point, in a position to receive target particles and other constituents which are transferred from the sampling point.

In certain embodiments, the constituents enter a first opening 14 of conduit 12 and are transferred the length of the conduit by negative pressure created by vacuum, exiting through second opening 16 via inlet 18 into at least one separator 15. The movement of constituents which causes their transfer in this way is responsive to a pressure gradient from an area of higher pressure to lower pressure. This pressure gradient causes the gas and at least some constituents from the sampling point to be drawn into the at least one separator 15 and ultimately into a contactor 25, as described herein. The particles may be either solid or liquid. As desired by a user, a single sampling point may be utilized, while in some embodiments multiple sampling points are utilized.

Generally, the suction created by the vacuum should be sufficient to create a centrifugal force on the aerosolized particles, including in the outermost separator, generally with respect to all constituents and particularly with respect to the target particles. Preferably, the vacuum is generated by a variable speed fan allowing adjustment for factors such as the number and volume of the separators, as well as the respective densities of the constituents including target particles.

Turning to FIG. 3, the at least one separator 15 is in fluid communication with contactor 25 through contactor opening 17. In certain embodiments, contactor opening 17 is an orifice formed through the outer wall surface of contactor 25. It will be appreciated that, in cases where a plurality of separators is used, e.g., FIG. 4B, one is the outermost separator and the other(s) are interior separators. The outermost separator includes inlet 18, while every other separator will have an interior separator opening 19 providing fluid communication between the outermost separator and each successive separator moving interiorly and ultimately to contactor 25.

The separators 15 thus separate constituents from the sampling point 20 based on the respective sizes and densities of the constituents. Based on their sizes and densities, a first subset of constituents (or, fraction) will pass through contactor opening 17 for the type of configuration shown in FIG. 4A, while a second fraction of constituents will not. In general, the more random the movement of the constituents, and thereby the more random the collisions of these particles with matter inside the at least one separator 15, the less effective the separation. Accordingly, geometry of the separator and inlet, as well as geometry and positioning of each interior separator opening 19 determine the gas movement pattern within the two or more separators and contactor and are thereby used to influence the movement of target particles and other constituents after they are transferred from the sampling point. For example, establishing a gas movement pattern as described herein allows for one separation to occur (e.g., FIG. 4A), or a series of separations (e.g., FIG. 4B), each of which separates relatively smaller or less dense constituents from larger or more dense constituents, with those entering contactor 25 being of the smallest size and/or the lowest density. The use of a plurality of separators provides flexibility to the approach. For example, and merely for illustration, one separator 15 with one contactor 25 can be configured with other system components described herein to separate 500 μm constituents from those which are on the order of millimeters. By comparison, a series of separations can be achieved with a configuration such as shown in FIG. 4B, resulting in three different fractions of constituents. Again, for illustrative purposes only, the system may be configured to allow a fraction with a diameter less than about 300 μm to pass ultimately through contactor opening 17 and into contactor 25. This fraction may be separate from a second fraction of constituents between about 300 μm and 500 μm, wherein the system can be configured in such a way that these constituents would pass through opening 19 and into the interior separator, but not into the contactor due to their relatively larger size and greater density than the under 300 μm fraction. And both of the aforementioned fractions may be separate from a third fraction of constituents greater than about 500 μm that remains in the outermost separator, the latter fraction having not been able to pass through opening 19 due to the exertion of greater centrifugal force on these relatively larger and more dense constituents.

When a plurality of separators is utilized, any one or more of the interior separator(s) can also be configured with an outlet and utilized as a contactor. Thus, in the previous illustration, the components of the system can be configured so that carrier liquid from reservoir 40 is introduced into an interior separator to transfer constituents of the approximately 300-500 μm fraction, which can be dispensed into their own collection vessel.

For example, in certain embodiments, a plurality of coaxial separators 15 having a common axis, with each separator being progressively smaller in size than the adjacent one moving inward. For example, as shown in FIG. 4B, the circumference and, therefore, the volume of each separator decreases as one moves from the outermost separator toward the contactor 25 located in the center. Thus, in certain embodiments, such a configuration permits only some of the aerosolized constituents, including target particles, to move in series through one or more separators (beginning with the outermost separator associated with inlet 18) and finally into the contactor. By way of example, FIG. 3 shows the respective positions of contactor opening 17 and inlet 18, which in some embodiments is rotatably adjustable into various configurations as discussed herein. Alternatively, the positions of the separator(s) and contactor (and, therefore, their respective inlet or openings) can be set at the time of manufacture.

Persons having ordinary skill in the art will appreciate the effect of centrifugal force on particles inside the separator. The density of each constituent that enters the separator determines the centrifugal force exerted upon that particle.

The relationship between density and centrifugal force determines which constituents enter contactor 25 through contactor opening 17, and which do not. Conversely, absent a centrifugal gas movement pattern inside the separator, collisions would be generally random and the respective densities of the particles would have less influence in determining which particles proceeded to the next separator moving inwardly (and ultimately to the contactor moving inwardly). However, as can be appreciated from various figures including FIG. 2, such a gas movement pattern in the separator(s) urges larger particles toward the periphery, and thus any probability of their entering the contactor (or the next separator moving inwardly) is highly remote if not impossible. Conversely, particles that are less dense have less momentum and the centrifugal force is less than for particles having greater density. Therefore, the smaller particles have the potential to pass through an interior separator opening 19 leading to the interior of the next separator moving inwardly (or, the contactor), while the larger ones do not.

As seen in FIG. 4B, in certain embodiments the at least one separator comprises a plurality of separators, each having inner and outer wall surfaces. The scope of embodiments is not limited by how many separators are employed. Although the figure includes two separators in combination with a single contactor, the embodiments described and/or claimed herein are not limited by the number of separators nor by the number of contactors. Aside from the outermost separator, in certain embodiments each of the openings 18, 19 to the separator(s) as well as contactor opening 17 into the contactor comprise a chamfered edge sloping inwardly, i.e., toward the interior space within the inner walls of the separator (or contactor, as the case may be). In FIG. 4B, the positioning of the interior separator opening is denoted by the reference numeral 19, and the general appearance and formation of this opening is similar to that of contactor opening 17 as shown in other drawing figures, particularly FIG. 5, and as discussed in the next paragraph.

The use of chamfered edges reduces turbidity at the entry point into the separator(s) and/or to the contactor, making the passage of constituents more fluid and aerodynamic. The inlet 18, the opening(s) 19 of the interior separator(s) and the contactor opening 17 are formed in any of a variety of ways as are known to person of skill in the art of manufacturing cylindrical or other objects having a material thickness, e.g., through post-fabrication machining or by forming them integrally during additive processes such as 3-D printing.

Figure 6:
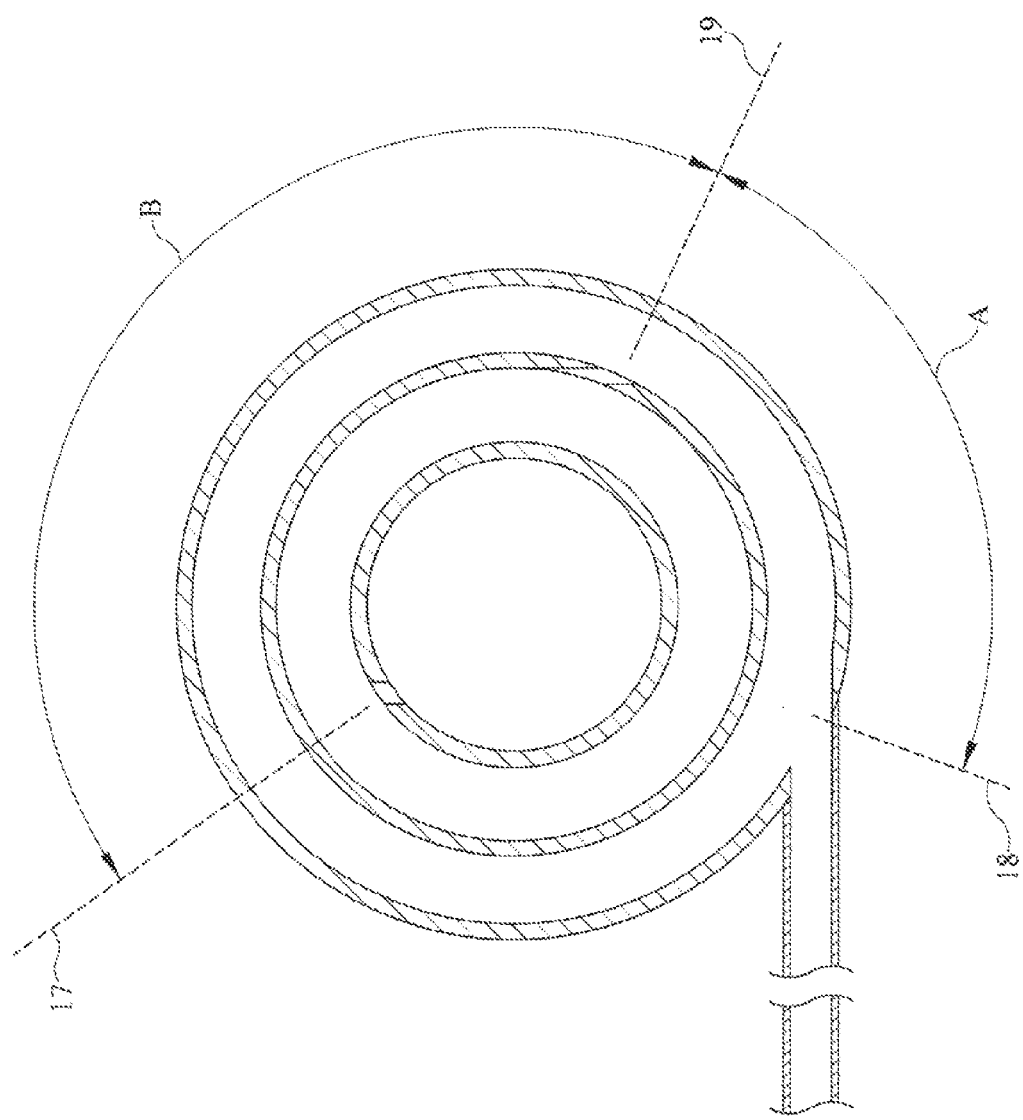
FIG. 6 is a perspective view of an aerosol particle separation and collection system having a plurality of separators that are coaxial with each other and with a contactor, according to multiple embodiments and alternatives.

In certain embodiments, the positioning of each interior separator opening 19 and inlet 18 is adjustable by rotating the contactor relative to the at least one separator(s), or by rotating at least one separator relative to the contactor, making the relative angular positioning of the openings selective for which constituents are separated out. FIG. 6 shows inlet 18 and interior separator opening 19, the positioning of which is set according to an adjustable alignment configuration. In the figure, the relative positioning of inlet 18 and opening 19 of an interior separator are represented by turn "A." Likewise, opening 19 and contactor opening 17 are also set according to an alignment configuration, as represented by turn "B," with all of these positions being rotatably configurable by turning the separator for angular adjustment as selected by a user. Manual adjustment as well as other mechanical options as known in the art exist for imparting relative rotation of the contactor relative to the at least one separator(s) or any one separator relative to at least one other separator.

In turn, the selected positions are held in place by configuring the separator(s) and contactor to maintain an interference fit through friction forces, thus holding them in substantially static positions as selectably desired until readjustment. In certain embodiments employing a plurality of separators, an interference fit is configured between, for example, the outermost separator and the interior separator positioned closest to the outermost separator. Such a fit is achieved through the implementation of friction forces according to any of a number of design choices which are known in the art. In some embodiments, positioning of the inlet relative to one or more openings is staggered as shown in FIG. 6 and is adjustable to allow multiple variations for how any given interior separator(s) and contactor can be rotated around axis 24 to increase the specificity of separations based on particle density.

In certain embodiments, various system components such as fan 11 are configured and effectuated with use of a controller 45 which may include a processor having a memory and program instructions for receiving inputs and executing firmware and/or software commands to control various elements of separation and collection as disclosed herein. In certain embodiments, memory for storage of data comprises RAM of any processor, or storage may be provided on disc, optical media, magnetic media, semiconductor memory devices, flash memory devices, mass data storage device, and other storage as is known in the art. In some embodiments, controller 45 includes one or more general or special purpose microprocessors, or any one or more processors of any kind of digital computer, including ones that sense conditions and perform various threshold comparisons. In some embodiments, controller 45 is coupled to user interface screens, key pads, and the like for entering and viewing information about the configuration and performance of system components. As desired, controller 45 may be connected to a network, e.g., local area network, private network, wide area network, and internet to name a few.

Although referred to as a single device, optionally the controller may be provided as several individual controllers or microprocessors, some or all of which may be centrally controlled by a personal computer or similar device. If desired, the vacuum and other system components are manually configured and operated.

In certain embodiments, a pump (not shown) for delivering the carrier liquid to the contactor is a positive displacement pump, such as a peristaltic pump or piston-driven, as are known to persons having ordinary skill in the art. Typically, the carrier liquid is stored in a reservoir 40 configured for holding carrier fluid which is delivered to the contactor. Reservoir 40 is joined to a channel 41 for establishing fluid communication with contactor 25. In certain embodiments, as shown in FIG. 1A, channel 41 comprises tubing connected to the reservoir and the contactor and configured to provide carrier liquid to contactor 25 directly via contactor inlet 28. Channel 41 may be configured with various fluid ports and gaskets at both reservoir and contactor ends, as may be desired. In some embodiments, a flow regulator (not shown) governs the movement of concentrated sample through tubing, both in terms of movement from the reservoir into contactor 25 or from the contactor into collection vessel 42. In some embodiments, controller 45 is configured to control the rate of flow by actuating the flow regulator and a liquid pump configured to transfer carrier liquid from the reservoir to the contactor. As may be suitable, various fittings, gaskets, valves, and shutoffs are provided in association with such a flow regulator. Optionally, the pH of the carrier liquid within the reservoir is maintained to a desired level using a buffer added to the liquid.

Inside the contactor, generally the carrier liquid level is maintained to a level higher than the contactor opening 17 through which constituents enter the contactor 25. In certain embodiments, the level is maintained with the use of an appropriate sensor as is known to those of ordinary skill in the art. Appropriate sensors may include, but are not limited to, capacitive, inductive, resistive, ultrasonic, infrared, and optical sensors that function to detect the level of fluid within the contactor. As desired, multiple sensors may be employed to determine and maintain the carrier liquid level. When this level drops below a certain predetermined threshold, additional carrier liquid is added to the contactor from the reservoir via the aforementioned tubing. Generally, evaporation is the primary factor that may cause the carrier liquid level to drop. Seepage from the contactor via contactor opening 17 is minimal or non-existent because of the centrifugal forces on the liquid due to the gas movement pattern and the chamfered orientation of the opening.

In an example operation, and with general reference to FIG. 1B, FIG. 2, FIG. 3, and FIG. 5 except where noted, constituents are transferred from a sampling point 20 as they enter a first opening 14 of conduit 12, by virtue of the vacuum emanating from the contactor 25. In some embodiments, due to negative pressure from the vacuum, the constituents then enter the chamber 21 of at least one separator 15 via the inlet 18, the second space being defined by the outermost one of the at least one separator 15. Within chamber 21, the constituents are subjected to centrifugal movement away from the center, which is represented by axis 24, thus undergoing separation according to the particles' respective densities. As desired, multiple separations are employed by adding interior separators 15 (see FIG. 4B) between the outermost separator 15 and the contactor 25. Moving inward, negative pressure from the vacuum ultimately draws some constituents including target particles into the contactor 25 via opening 17, to be dispersed in the carrier liquid and then to exit the contactor via outlet 27. As depicted in FIG. 1A, tubing 43 is also represented by dashed lines and in some embodiments represents standard tubing having an opening at each of a first end, which communicates with the contactor via outlet 27, and a second end, which communicates with collection vessel 42.

Each of the various structures described herein according to multiple embodiments and alternatives is formed from a range of materials, as may be selected by a user and which will be readily apparent to those of skill in the art to which the present disclosure applies. Materials may be selected, for example, according to desired firmness and rigidity, durability, weight, and inertness with liquid or gas chemicals (e.g., the constituents including target particles, or the buffered liquid) coming in contact with surfaces, with polyethylene being an exemplary material. All materials described herein can be transparent, semitransparent, or opaque according to user decision and implementation.

It is to be understood that the embodiments described and/or claimed herein are not limited in their application to the details of the teachings and descriptions set forth herein, or as illustrated in the following examples. Rather, it will be understood that the embodiments are capable of being practiced or carried out in multiple ways, according to many alternatives based on these descriptions and teachings.

Further, it will be understood that the phraseology and terminology used herein is for the purpose of description and should not be regarded as limiting. The use herein of "including," "comprising," "e.g.," "such as, for example," "containing," or "having" and variations of those words is meant in a non-limiting way to encompass the items listed thereafter, and equivalents of those, as well as additional items. Accordingly, the foregoing descriptions are meant to illustrate a number of embodiments and alternatives, rather than limiting to the precise forms and processes disclosed herein. The descriptions herein are not intended to be exhaustive. It will be understood by those having ordinary skill in the art that modifications and variations of these embodiments are reasonably possible in light of the above teachings and descriptions.

What is claimed is:

1. A particle separation and collection system, comprising:

a conduit for transferring constituents from a sampling point to at least one separator, the conduit comprising a first opening and a second opening, the conduit defining a substantially closed transfer path from the sampling point to at least one separator;

the at least one separator comprising a chamber with a curved inner wall surface and an inlet joined to the second opening of the conduit, wherein the conduit and second conduit opening are positioned tangentially to a central axis of the at least one separator;

a contactor having an outer wall surface, wherein the contactor is positioned coaxially with and substantially within the at least one separator and the contactor defines a contact space, the contactor further comprising a contactor opening for receiving constituents and an outlet for establishing fluid communication with a collection vessel; and a reservoir with a channel establishing fluid communication between the reservoir and the contactor.

2. The system of claim 1, wherein the inlet of the at least one separator defines a chamfered edge sloping inwardly, for directing constituents toward the contactor outer wall surface.

3. The system of claim 1, wherein the at least one separator comprises a plurality coaxial separators, with an outermost separator surrounding at least one interior separator, wherein the at least one interior separator comprises an opening for receiving constituents.

4. The system of claim 3, wherein the inlet of each separator defines a chamfered edge sloping inwardly toward the interior of the separator.

5. The system of claim 1, wherein the inner wall surface is circular.

6. The system of claim 1, further comprising a vacuum configured to generate a negative pressure within the at least one separator and the contactor, the negative pressure transferring constituents from the sampling point to the at least one separator and then to the contactor.

7. The system of claim 1, wherein the contactor comprises a substantially enclosed space configured to receive a carrier liquid.

8. The system of claim 7, further comprising a liquid pump configured to transfer carrier liquid from the reservoir to the contactor, and further comprising a flow regulator.

9. The system of claim 8, further comprising a sensor for sensing the volume of carrier liquid in the contactor.

10. The system of claim 9, further comprising a controller configured to communicate with the sensor and flow regulator, the sensor being configured to sense carrier liquid volume in the contactor, the controller having a processor for executing machine-readable instructions and receiving carrier liquid volume data from the sensor, and for adjusting the flow regulator when the volume is below a threshold.

11. The particle separation and collection system of claim 1, wherein an angle formed between the contactor opening relative to the inlet and a distance between the contactor opening and the inlet are adjusted, by rotating the contactor relative to at least one separator, to determine which constituents enter the contactor.

12. The particle separation and collection system of claim 11, wherein the contactor and at least one separator are circular.

* * * * *